United States Patent [19]

Henry et al.

[11] 4,026,898
[45] May 31, 1977

[54] 7-OXO-1,2,3,3,8-PENTAMETHYL-5-TRI-FLUOROMETHYL-2,3,7,8-TETRAHYDRO-1-H-PYRROLO[3,2-g] QUINOLINE, A STABLE, EFFICIENT LASER DYE

[75] Inventors: Ronald A. Henry, China Lake; Peter R. Hammond, Livermore; Erhard J. Schimitschek, San Diego; John A. Trias, La Mesa, all of Calif.

[73] Assignee: The United States of America as represented by the Secretary of the Navy, Washington, D.C.

[22] Filed: Mar. 4, 1976

[21] Appl. No.: 663,887

[52] U.S. Cl. .............. 260/288 CF; 260/326.11 R; 331/94.5 L
[51] Int. Cl.² ...................................... C07D 471/04
[58] Field of Search .................... 260/288 CF

[56] References Cited
UNITED STATES PATENTS

| | | |
|---|---|---|
| 3,005,824 | 10/1961 | Domagk et al. ............. 260/288 CF |
| 3,649,634 | 3/1972 | Fujimura et al. ............ 260/288 CF |

*Primary Examiner*—R. Gallagher
*Attorney, Agent, or Firm*—R. S. Sciascia; Roy Miller; David J. Aston

[57] ABSTRACT

7-Oxo-1,2,3,3,8-pentamethyl-5-trifluoromethyl-2,3,7,8-tetrahydro-1-H-pyrrolo[3,2-g] quinoline, a new compound, useful as a blue-green laser dye, is prepared from a substituted indole. It has the expanded formula

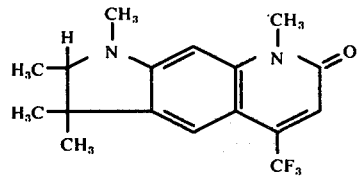

3 Claims, No Drawings

7-OXO-1,2,3,3,8-PENTAMETHYL-5-TRI-FLUOROMETHYL-2,3,7,8-TETRAHYDRO-1-H-PYRROLO[3,2-G] QUINOLINE, A STABLE, EFFICIENT LASER DYE

BACKGROUND OF THE INVENTION

This invention relates to laser dyes and to the preparation of such dyes. More particularly, this invention relates to a dye of the substituted quinoline class having a rigidized heterocyclic nitrogen atom.

Although a relatively recent advance, the use of liquid organic laser media has been the subject of widespread research. Research has been stimulated by a number of advantages inherent in the use of laser dyes. They generally are capable of laser emission over a wide range of wavelengths, and, using optical techniques, may be tuned to certain specific wavelengths. Compared to gaseous and solid laser media, the dyes are more economical, and do not suffer from cracks or other optical imperfections. Also, a wide range of different organic dyes are available.

Among the first class of compounds found to be efficient laser dyes were the coumarins. See, for example, Schimitshek et al., *Optics communications*, Vol. II, p. 352 (1974); Reynolds et al., *Optics Communications*, Vol. 13, p. 222 (1975). It is known that substituents affect important characteristics of the dyes, such as emission spectrum, yield efficiency, and threshold of excitation. Experimentation with various substituents led to the exploration of quinoline derivatives as a class of dyes. For instance, Drexhage in U.S. Pat. No. 3,873,940 reports that a rigidized heterocyclic nitrogen ring produces a more efficient laser emission. Schimitshek et al., supra, report that the addition of a triflouromethyl group improves the stability of the dye, which to date has been a major problem, in that the optical excitation used to generate laser emissions tends to break down the active components of the molecule, a process termed "bleaching."

SUMMARY OF THE INVENTION

A compound having the formula

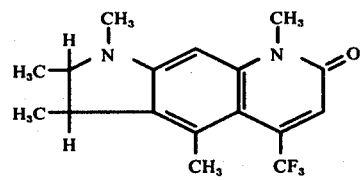

is prepared from a substituted indole (Fischers' base) by a series of steps comprising reduction by $H_2$ with a charcoal-palladium catalyst, adding a nitro group by $HNO_3$, reducing the group to $NH_2$ and the addition of a ring and a trifuloromethyl group by ethyl trifluoroacetoacetate and the conversion of the amide group to —N—$CH_3$ by trimethyl phosphate. The compound thus produced is an efficient and a stable dye which lases in the blue-green region, an important advantage in that light if this frequency is transmitted by seawater.

DESCRIPTION OF THE PREFERRED EMBODIMENT

The synthetic path of the disclosed compound may be represented diagrammatically as follows:

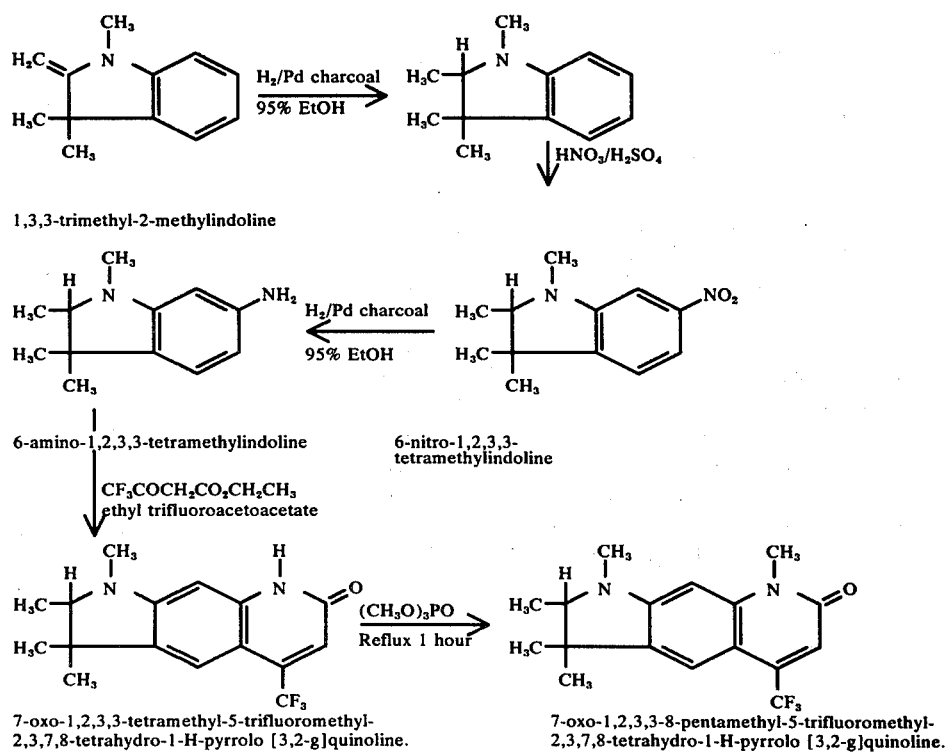

In one instance the reactions were carried out as follows:

6-Amino-1,2,3,3-tetramethylindoline 1,3,3-Trimethyl-2-methyleneindoline (Fischer's base) (35 g, 0.2 mole) in 100 ml of 95% ethanol was hydrogenated over 0.5 g of 10% Pd on charcoal. The initial pressure was 50 psi; the theoretical uptake of hydrogen required only 15 minutes. The catalyst was removed by filtration and washed twice with ethanol; the combined filtrates were evaporated to leave 35.1 g of pale orange liquid.

All of the above liquid was added dropwise over 30 min. to 200 ml of 96% sulfuric acid with good stirring and cooling to maintain a temperature of 8–10° C. Then 9 ml of 90% nitric acid (d = 1.5 g/cc) in 200 ml of cold 96% sulfuric acid was added over 1 hour, again with good agitation and cooling to keep the temperature 2°–4° C. After stirring for 1 hour more, the nitration mixture was poured over 1000 g of ice and neutralized with solid sodium carbonate. The orange solid which separated was filtered and washed well with cold water. The yield of dried product was 42.1 g (96%).

The crude 6-nitro-1,2,3,3-tetramethylindoline was dissolved in 140 ml of hot n-hexane; the solution was filtered from a trace of dark flocculent material and cooled to 5° C. The orange crystalline solid was removed, washed with cold hexane and dried, 34 g; mp 59–60° C.

Some of the previous nitro compound (8.2 g, 0.037 mole) was reduced in 70 ml of 95% ethanol over 0.35 g of 10% Pd on charcoal. The pressure drop from 50 psi was rapid; the uptake of hydrogen corresponded to the theoretical 0.11 mole. After removing the catalyst, the solvent was evaporated under reduced pressure to leave 6.9 g of oil. The 6-amino-1,2,3,3-tetramethylindoline, which darkened rapidly upon exposure to air, was used immediately without further purification for the next preparation.

7-oxo-1,2,3,3-tetramethyl-5-trifluoromethyl-2,3,7,8-tetrahydro-1H-pyrrolo [3,2-g] quinoline 6-Amino-1,2,3,3-tetramethylindoline (6.9 g, 0.036 mole) was treated with 6.8 g of ethyl trifluoroacetoacetate. There was an immediate reaction with heat evolution and formation of a solid. The mixture was heated in an oil bath under a reflux condenser for 16 hrs at 135°–140° C, then for 1 hr at 145°–150° C. The cooled cake was broken up, triturated with 10 ml of diethyl ether, filtered and washed twice with cold ether; 7.7 g (69%). When recrystallized from 275 ml of 95% ethanol, the compound was obtained as felted, yellow needles; m.p. 248°–249° C, shrinking at 244° C.

Analysis showed: Calcd. for $C_{16}H_{17}F_3N_2O$: C, 61.92; H, 5.52; N, 9.03; Found: C, 61.26; H, 5.56; N, 8.85.

7-Oxo-1,2,3,8-pentamethyl-5-trifluoromethyl-2,3,7,8-tetrahydro-1H-pyrrolo [3,3-g] quinoline The quinolone II (10 g, 0.032 mole) was refluxed in trimethyl phosphate (100 ml) for an hour, the mixture cooled to −15° and 9.4 g (65%) of the methyl quinolone III filtered off. Dilution with water gave no further material. Recrystallization from methanol/water using decolorizing charcoal gave yellow needles; m.p. 176.5°–177° C. Nuclear magnetic resonance and infrared spectra were in accord with the proposed structure.

Analysis showed: Calcd. for $C_{17}H_{19}F_3N_2O$: C, 62.9; H, 5.86; N, 8.64; F, 17.6; Found: C, 63.0; H, 5.90; N, 8.49; F, 17.8.

The compounds above described as "quinolone II" and "quinolone III" are both efficient laser dyes, although quinolone II is of lower output and stability than quinolone III. They are suitable for use in a variety of polar solvents, such as ethanol and in a variety of liquid laser equipment, for example the AVCO Everett Research Laboratory, Inc. C400 nitrogen laser/Dial-a-Line laser combination.

What is claimed is:
1. 7-Oxo-1,2,3,3,8-pentamethyl-5-trifluoromethyl-2,3,7,8-tetrahydro-1-H-pyrrolo [3,2-g] quinoline.
2. 7-Oxo-1,2,3,3-tetramethyl-5-trifluoromethyl-2,3,7,8-tetrahydro-1-H-pyrrolo [3,2-g] quinoline.
3. A method for preparing 7-oxo-1,2,3,3,8-pentamethyl-5-trifluoromethyl-2,3,7,8-tetrahydro-1-H-pyrrolo [3,2-g] quinoline comprising the steps of:
   a. hydrogenating under pressure 1,3,3-trimethyl-2-methylindoline with a 10% palladium on charcoal catalyst whereupon the catalyst is removed leaving a liquid;
   b. forming a reaction mixture by adding with cooling and stirring to said liquid nitric acid and sulfuric acid, whereupon the reaction mixture is neutralized to obtain 6-nitro-1,2,3,3-tetramethylindoline;
   c. reducing said 6-nitro-1,2,3,3-tetramethylindoline to the corresponding 6-amino-1,2,3,3-tetramethylindoline;
   d. reacting then refluxing said 6-amino-1,2,3-tetramethylindoline with ethyl trifluoroacetoacetate to yield 7-Oxo-1,2,3,3-tetramethyl-5-trifluoromethyl-2,3,7,8-tetrahydro-1-H-pyrrolo [3,2-g] quinoline; and
   e. refluxing said 7-oxo-1,2,3,3-tetramethyl-5-trifluoromethyl-2,3,7,8-tetrahydro-1H-pyrrolo [3,2-g] quinoline with trimethyl phosphate to yield 7-oxo-1,2,3,3,8-pentamethyl-5-trifluoromethyl-2,3,7,8-tetrahydro-1H-pyrrolo [3,2-g] quinoline.

* * * * *